United States Patent [19]

Hassett

[11] Patent Number: 5,131,266
[45] Date of Patent: Jul. 21, 1992

[54] METHOD AND APPARATUS FOR CONTINUOUSLY MEASURING THE CONCENTRATION OF ORGANIC COMPOUNDS IN AN AQUEOUS SOLUTION

[75] Inventor: John P. Hassett, Cortland, N.Y.

[73] Assignee: The Research Foundation of the State University of New York, Albany, N.Y.

[21] Appl. No.: 583,400

[22] Filed: Sep. 17, 1990

[51] Int. Cl.⁵ .............................................. G01N 1/18
[52] U.S. Cl. ................................ 73/61.41 R; 210/644
[58] Field of Search ............. 73/61.1 R, 61 R, 61.1 C, 73/53; 210/644, 640

[56] References Cited

U.S. PATENT DOCUMENTS

| | | | |
|---|---|---|---|
| 3,929,003 | 12/1975 | Llewellyn | 73/61.1 R X |
| 4,775,476 | 10/1988 | Melcher et al. | 210/635 |
| 4,912,051 | 3/1990 | Zaromb | 436/178 |
| 4,913,821 | 4/1990 | Melcher et al. | 210/635 |
| 4,976,869 | 12/1990 | Taylor | 210/644 |
| 5,024,929 | 6/1991 | Loughheed et al. | 210/644 X |
| 5,059,327 | 10/1991 | Takegami | 210/640 X |

OTHER PUBLICATIONS

Melcher, R. G., "Flow-Injection Determination of Membrane-Selected Organic Compounds", Analytica Chimica Acta, 214, (1988), pp. 299-313.

*Primary Examiner*—Hezron E. Williams
*Assistant Examiner*—Joseph W. Roskos
*Attorney, Agent, or Firm*—Heslin & Rothenberg

[57] ABSTRACT

A system for continuously measuring the concentration of organic compounds in an aqueous solution utilizes a first non-porous hollow fiber bundle having organic solvent flowing therethrough to extract organic compounds from a water sample into the organic solvent. The extractant can then flow through a second hollow fiber bundle where pervaporation of a fraction of the solvent takes place thereby increasing the concentration of organic compounds in the solvent extractant. The extractant then flows into a control unit which identifies and quantifies the organic compounds therein.

15 Claims, 2 Drawing Sheets

METHOD AND APPARATUS FOR CONTINUOUSLY MEASURING THE CONCENTRATION OF ORGANIC COMPOUNDS IN AN AQUEOUS SOLUTION

GOVERNMENT RIGHTS

This invention was made with Government support under Contract No. R814407020 awarded by the Environmental Protection Agency. The Government has certain rights in this invention.

BACKGROUND OF THE INVENTION

This invention relates to the field of testing for the concentration of organic compounds in liquids, and more particularly, to a method and apparatus for continuously measuring the concentration of organic compounds in an aqueous solution.

Considering the present environmental problems involving both waste disposal and its effect upon the quality of water, it is necessary to test groundwater, water supplies, waste water and/or industrial liquid waste to determine the concentration of any contaminants therein. It is desirable to continuously measure liquids for the concentration of organic compounds in order to minimize the deleterious effects of these contaminants in water and to maintain and improve the quality of our water supplies. Many non-purgable hydrophobic organic compounds are known to contaminate water supplies. Polychlorinated biphenyls (PCBs), polynuclear aeromatic hydrocarbons (PAHs), dioxins, petroleum materials, and pesticides, for example, are just some of these commonly known organic compounds.

There are currently available modern analytical instruments which are capable of detecting and quantifying minute amounts of organic compounds. Presently, however, the testing of water and other liquid solutions for the presence of organic compounds is commonly performed in a non-continuous, non-real time manner where samples of water are transported to various testing apparatuses. This procedure, however, is labor intensive and is usually performed in the laboratory.

One problem with the current testing and measurement of organic compounds in water is that the concentration of these organic compounds in water may be minute making it difficult for analytical devices to accurately measure the concentration levels. As a result, it is frequently necessary to increase the concentration of the organic compounds in order to measure their concentration. In these situations, an organic solvent extract containing organic compounds is typically evaporated off-line and then analyzed to determine concentration levels. Hollow fiber membranes have been used in industrial extractors and pervaporators. However, it is desirable to utilize a system which operates as an analytical sampler/extractor/concentrator to provide continuous on-line measurements of the concentration of organic compounds utilizing non-porous hollow fibers.

It is, therefore, an object of the present invention to provide a method and apparatus for measuring the concentration of organic compounds in aqueous solutions which can be accomplished in the field.

It is also an object of the present invention to provide an apparatus for measuring the concentration of organic compounds which will provide a real-time, on-line continuous measurement of the concentration of organic compounds in water, waste water and industrial liquid waste.

It is also an object of the present invention to provide a method and apparatus for measuring the concentration of organic compounds in an aqueous solution which may provide accurate and reliable measurements of the concentrations of such organic compounds.

SUMMARY OF THE INVENTION

The aforementioned objects are achieved through implementation of the method and apparatus for measuring the concentration of organic compounds in an aqueous solution in accordance with the present invention.

The apparatus includes a first hollow fiber bundle, means for allowing the outer surface of the first hollow fiber bundle to be placed in fluid flow relationship with an aqueous solution containing organic compounds therein; a second hollow fiber bundle mountable in series with the first hollow fiber bundle; means for allowing an organic solvent to flow through the first hollow fiber bundle and then through the second hollow fiber bundle; means for pervaporating solvents flowing through the second hollow fiber bundle to increase the concentration of organic compounds in the solvent; means for measuring the flow rate of a solvent which has exited the second hollow fiber bundle; and means for measuring the concentration of organic compounds in the solvent.

The apparatus may further comprise a pump for forcing solvents through the first and second hollow fiber bundles, a means for monitoring the flow rate of an organic solvent flowing through the first bundle, a sampling pump, and/or a gas sweep means for flowing gas over the second hollow fiber bundle to enable solvent therein to diffuse through the second hollow fiber bundle and vaporize in the gas while preventing organic compounds from diffusing therethrough. The pump and the means for measuring the flow rate of organic solvent flowing through the first bundle may be a metering pump and the gas sweep means may comprise an air pump. The means for pervaporating an organic solvent may comprise a vacuum means for creating low pressure on the outer side of the second hollow fiber bundle and the means for measuring the concentration of organic compounds in the solvent may comprise a gas chromatograph or ultra violet absorbance monitor.

The invention also includes a process for continuously measuring the concentration of organic compounds in an aqueous solution including placing the outer surface of a first hollow fiber bundle in fluid flow relationship with an aqueous solution, flowing an organic solvent through the hollow fiber bundle thereby extracting organic compounds from the liquid into the solvent, pervaporating the organic solvent to increase the concentration of organic compounds therein, measuring the flow rate of the solvent after concentration of the organic compounds therein has been increased, measuring the concentration of one or more of the organic compounds in the solvent, and calculating the concentration of one or more organic compounds in the sampled aqueous solution.

Pumping an aqueous solution to be sampled into the outer surface of the first hollow fiber bundle may be performed while the flow rate therein is measured. The organic solvent may be pumped, at a preselected flow rate through the first and second hollow fiber bundles. Pervaporating the organic solvent may be accomplished by flowing the organic solvent through a second hollow fiber bundle having a gas sweep on the outside thereof to enable solvent to diffuse through the tubes while preventing the organic compounds from diffusing therethrough. Pervaporating the organic solvent could also be accomplished by flowing the organic solvent through the second hollow fiber bundle maintained under a vacuum to enable solvent to diffuse through the membrane while preventing the organic compounds from diffusing therethrough.

The system may be used for testing water supplies, waste waters and industrial liquid wastes by continuously extracting organic compounds from a liquid into a flowing stream of solvent. The stream of solvent extract is then further concentrated and may be interfaced with a variety of analytical instruments to provide close to real-time identification and quantification of organic compounds. The process is capable of achieving high concentration factors while being fully automated, portable and operational at a sampling site.

BRIEF DESCRIPTION OF THE DRAWINGS

These and other objects, features and advantages of the invention will be evident from the following detailed description when read in conjunction with the accompanying drawing in which.

DETAILED DESCRIPTION OF THE PREFERRED EMBODIMENT

Figure 1:
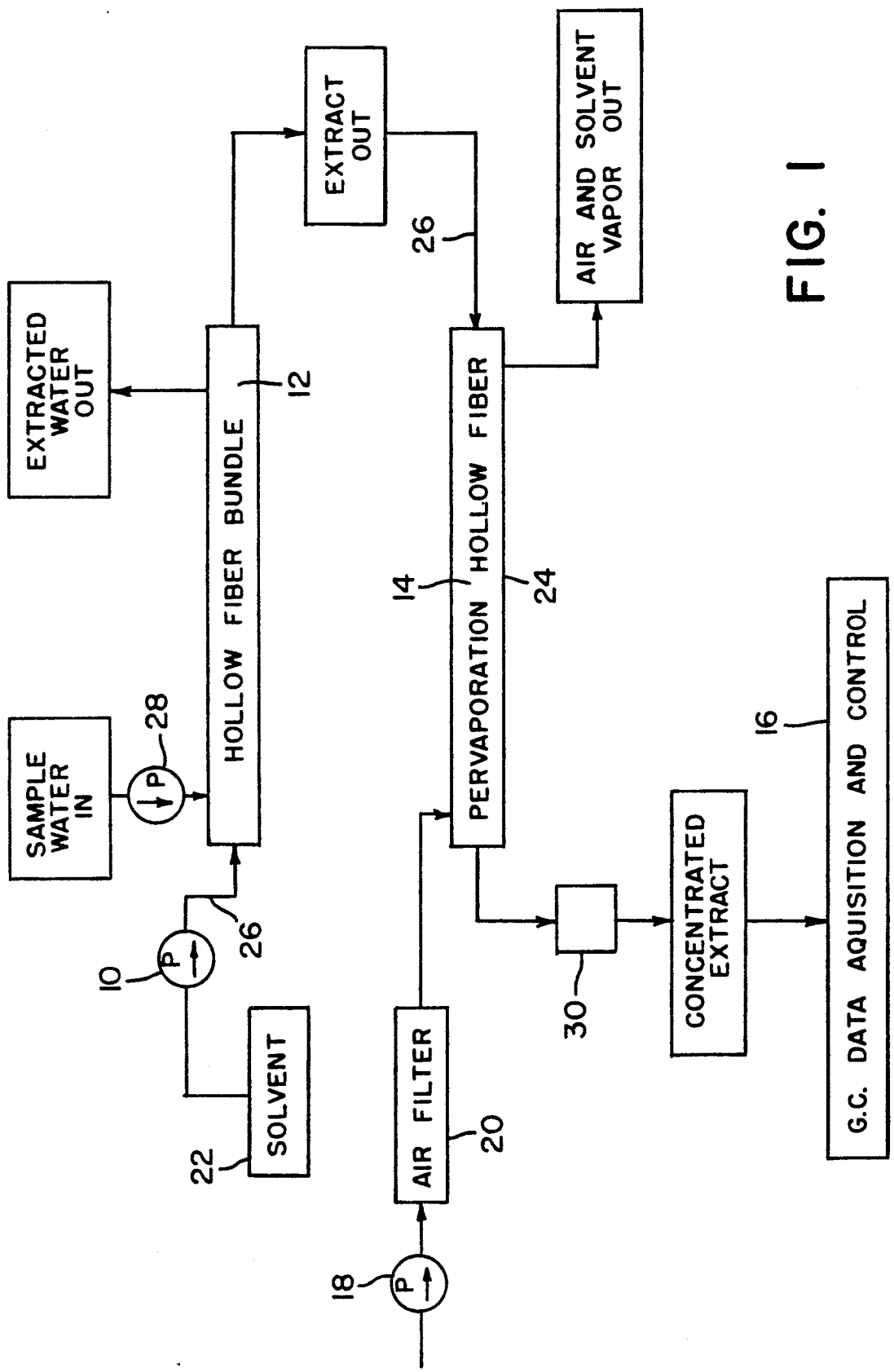
FIG. 1 is a schematic diagram of the apparatus for continuously measuring the concentration of organic compounds in a liquid assembled in accordance with the principles of the present invention.

Referring now to FIG. 1, in accordance with the present invention, an apparatus for continuously measuring the concentration of organic compounds in water contains a metering pump 10, a first hollow fiber bundle 12, a second hollow fiber bundle 14, a data acquisition and control unit 16, an air pump 18, an air filter 20, a sampling pump 28 and a solvent supply means 22.

The system is a continuous flow on-line extraction/concentration/analysis apparatus which extracts organic compounds from a sample of water into an organic solvent, concentrates the organic compounds within the solvent and analyzes the concentration to arrive at a measurement of the concentration level of the organic compounds in the water. The apparatus is configured in accordance with the diagram shown in FIG. 1. The first hollow fiber bundle 12 is in series fluid flow relationship with the second hollow fiber bundle 14. A means for flowing organic solvent through the hollow fiber bundles such as a pipe or tube network 26 allows organic solvent to flow from the first hollow fiber bundle 12 into the second hollow fiber bundle 14. A metering pump 10 is located within the flow network for controlling and monitoring the flow rate of organic solvent through the system. A data acquisition and control unit 16 is located in series with the second hollow fiber bundle 14. The second hollow fiber bundle 14 is encased within a housing 24 which is connected to an air supply pump 18 and air filter 20 which supplies clean air within the housing 24 surrounding hollow fiber bundle 14. A solvent supply means 22 supplies the entire system with an organic solvent which flows through the piping or tubing network via the metering pump 10.

Figure 2:
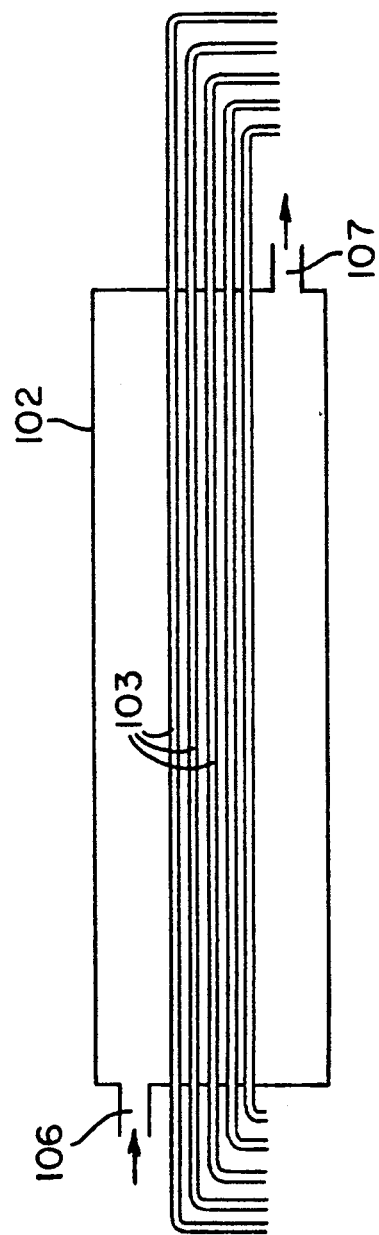
FIG. 2 depicts a conventional hollow fiber bundle useable in the present invention.

The first hollow fiber bundle or second hollow fiber bundle may be constructed as shown in FIG. 2. The hollow fiber bundle has one or more non-porous hollow fiber membrane tubes 103. Each tube runs through an outer shell 102. The shell contains an inlet 106 and an outlet 107. The first hollow fiber bundle in the system will have the aqueous solution flowing through the shell 102 around the tubes 103 while the second bundle in the system may have a gas such as air flowing within the shell 102. Although, FIG. 2 depicts one configuration of a hollow fiber bundle, many types of configurations will suffice for application in the present invention.

The first hollow fiber bundle 12 contains a plurality of non-porous hollow fiber polymer membrane tubes oriented to form a hollow fiber bundle 12. The tubes are made of a non-porous polymer membrane such as silicone rubber. It has been found, that the preferred materials for the tubes are polydimethylsiloxane and certain low density polyethylenes. The second hollow fiber bundle 14 can also be made of one or more non-porous hollow fiber polymer membrane tubes.

The data acquisition and control device 16 may comprise any commonly available types of analytical instruments to provide real-time identification and quantification of organic compounds. For example, liquid or gas chromatographs and ultra violet absorbance monitors may be used. The data acquisition and control device may also contain a microprocessor which converts the value of the concentration of the organic compounds in the solvent into the value of the concentration of the organic compounds in the water based upon certain parameters maintained and monitored by the control device. The air pump 18 is connected to the air filter 20 which leads into the housing 24. Any commonly available air pump will suffice for this application. The air filter 20 must be capable of removing any particles within the air which may adhere to the surface of the second hollow fiber bundle 14 and possibly impede the diffusion of solvent therethrough, and removing gaseous compounds which might otherwise permeate into the solvent and interfere with the analysis.

The system operates with the direction of solvent flowing as shown in FIG. 1. The metering pump 10 supplies solvent from the solvent supply means 22 into the piping network 26 which leads into the first hollow fiber bundle 12. Organic solvent, such as Hexane, Octane or Decane, then flows within the first hollow fiber bundle 12 and emerges therefrom as an extract containing a certain concentration level of organic compounds therein. Water from a supply to be sampled is pumped by means of a sampling pump 28 over the first hollow fiber bundle 12. Organic compounds within the water sample absorb to the surfaces of the hollow fiber tubes forming the hollow fiber bundle and diffuse through the membranes into the continuously flowing organic solvent inside each of the tubes. The hollow fiber bundle 12 may be placed in a chamber thereby enabling pumped water samples to flow over the individual tubes. The organic solvent flowing out of the first hollow fiber bundle 12 will then contain certain organic compounds therein which will flow into the second hollow fiber bundle 14 located within the housing 24.

The air pump 18 and air filter 20, in conjunction with the housing 24, form a gas sweep. The air pump 18 forces air to the housing 24 over the second hollow fiber bundle 14 enabling a fraction of the solvent to diffuse through the second hollow fiber bundle into the air within the housing to create an air and solvent vapor mixture which is then removed from the housing 24. While the organic solvent diffuses through the second hollow fiber bundle 14, the organic compounds within the solvent will not diffuse therethrough but instead remain within the residuary solvent thereby increasing the concentration of the organic compounds within the solvent. This process for increasing the concentration of the organic solvents, referred to as pervaporation, enables the data acquisition and control unit 16 to more accurately and reliably measure the concentration of the organic compounds.

As an alternative to a gas sweep, pervaporation may be achieved by creating a vacuum within the housing 24. In this embodiment of the apparatus, the air pump 18 may be reversed and the air filter 20 removed. The air pump then can be run at relatively low pressure to create a vacuum within the housing 24. The low pressure within the vacuum creates suction thereby removing the vapor from the housing 24 which facilitates the diffusion of solvent through the second hollow fiber bundle 14 into the housing 24.

A means for measuring the flow rate of the concentrated solvent extract 26 is included in the system after the second hollow fiber bundle 14 or within the control unit 16. Any conventional type of flow measuring means may be used. For example, the collected extract may be measured over a certain period of time to determine the flow rate. Conventional flowmeters may not be accurate if the flow of extract is light. Alternatively, a solvent mixture containing a combination of a fixed concentration of a nonvolatile solvent, such as Octane or Decane, with a volatile solvent, such as Hexane, may be used. The volatile solvent will vaporize during pervaporation and the flow rate of the extract will be equal to the percentage of the concentration of the nonvolatile solvent in the solvent mixture multiplied by the flow rate of the solvent mixture through the first hollow fiber bundle.

The system in accordance with the present invention may be operated in either a fast mode or slow mode. Operation of the system in the fast mode could conceivably result in non dissolved organic compounds not diffusing through the first hollow fiber bundle 12. Conversely, operation of the system in the slow mode may enable non dissolved organic compounds to diffuse through the first hollow fiber bundle 12 and become concentrated within the solvent. However, it has been found that the sensitivity of the system is improved when operated in the fast mode as compared to the slow mode.

Operation of the system in the fast mode can only occur under certain conditions which will be described herein. The flux of organic compounds through the membrane may be represented by the equation:

$$Jm = (DA/L)(K_w C_w - K_s C_s)$$

where Jm is the flux (mole/min), D is the diffusion coefficient (cm$^2$/min), A is the surface area of the membranes in the first hollow fiber bundle (cm$^2$), L is the thickness of the membrane in the first hollow fiber bundle (cm), $K_w$ and $K_s$ are the membrane-water and membrane-solvent partition coefficients, respectively (unitless), and $C_w$ and $C_s$ are the concentrations of the organic compounds in the water and solvent, respectively (mol/cm$^2$).

In the fast mode, the system is operated so that the value of $K_w C_w$ is much greater (typically 10 times greater) than the value of $K_s C_s$. This condition is typically obtained with a high flow rate of solvent, as controlled by the metering pump 10, through the first hollow fiber bundle 12. Also, the flux of the organic compounds in the water should be much greater (at least 10 times greater) than the flux of organic compounds through the membrane. This condition is most easily obtained with a high flow rate of water over the first hollow fiber bundle 12, as controlled by the sampling pump 28. When these conditions occur, the flux of organic compounds through the membrane may be represented by:

$$Jm = (DAK_w/L)C_w$$

During operation of the system, the flux of the organic compounds through the membrane is equal to the flux of the organic compounds through the solvent extract such that:

$$C_s = (1/F_s)Jm$$

where $F_s$ is the flow rate of the solvent exiting the second hollow fiber bundle (cm$^3$/min).

The relationship between the concentration of the organic compounds in the solvent and their concentration in the water can then be represented by:

$$C_s = (DAk_w/LF_s)C_w$$

Therefore, the concentration of the organic compounds in water can be obtained in the fast mode by measuring the concentration of the organic compounds in the solvent and measuring the flow rate of the solvent. The value $D K_w$ is a constant which can be experimentally measured prior to sampling by using known water concentration samples and solvent flow rates.

Operation of the system in the slow mode can be achieved when the flux of the organic compounds in the water, the flux of the compounds through the membrane and the flux of the compounds in the solvent are all equal. However, it is often impractical to require that 100% of the organic compounds in the water be absorbed into the membrane. It is sufficient to achieve satisfactory reliability if, for example, 95% of the compounds in the water are diffused through the membranes. This conditions can be achieved when the flow rate of the sample water one hundredths of the value of $(DAK_w/L)$, i.e., $F_w = 0.05 (DAK_w/L)$. By assuming that the flux through the solvent is equal to the flux through the water, in the slow mode, the concentrations are related by:

$$C_s = (F_w/F_s)C_w$$

Where $F_w$ is the flow rate of water over the first hollow fiber bundle 12. Therefore the concentration of the organic compounds in the water can be obtained, in the slow mode, by measuring the flow rate of both the water and the solvent exiting the second hollow fiber bundle 14 as well as the concentration of the organic compounds in solvent.

The system continuously extracts organic compounds from water into a flowing stream of solvent and then increases the concentration of the compounds within the solvents through pervaporation. The stream of solvent extract can be interfaced to a variety of analytical instruments to provide close to real-time identification and quantication of organic compounds within the supply of water sampled. The system is capable of achieving high concentration factors, is fully automated and portable, enabling it to be operated at the sampling site.

Although the system has been described with respect to water testing, the system may be used continuously to monitor surface water, ground water, or industrial process streams. By interfacing an appropriate data acquisition and control device for analysis, the system may be used to provide a continuous real-time indication of the organic compounds within a water sample and the concentrations thereof. Although the invention has been described with regard to the embodiments disclosed herein, variations in the system may be made without departing from the spirit of the invention. Any such variations are intended to be within the scope of the invention as defined by the following claims.

What is claimed is:

1. A process for continuously measuring the concentration of organic compounds in an aqueous solution comprising:

placing the outer surface of a first hollow fiber bundle comprising a set of one or more non-porous hollow fiber tubes in fluid flow relationship with an aqueous solution;

flowing an organic solvent through the first hollow fiber bundle thereby extracting organic compounds from the aqueous solution into the solvent;

pervaporating the organic solvent to increase the concentration of one or more organic compounds therein;

measuring the flow rate of the solvent after the concentration of the organic compounds therein has been increased;

measuring the concentration of one or more of the organic compounds in the solvent; and calculating the concentration of the organic compounds in the sampled aqueous solution.

2. The process for continuously measuring the concentration of organic compounds in an aqueous solution according to claim 1 wherein placing the outer surface of the first hollow fiber bundle in fluid flow relationship with an aqueous solution comprises pumping the aqueous solution into contact with said outer surface.

3. The process for continuously measuring the concentration of organic compounds in an aqueous solution according to claim 2 further comprising measuring the flow rate of the aqueous solution being pumped.

4. The process for continuously measuring the concentration of organic compounds in an aqueous solution according to claim 2 wherein the organic solvent is pumped, at a preselected flow rate, through the first hollow fiber bundle and a second hollow fiber bundle.

5. The process for continuously measuring the concentration of organic compounds in an aqueous solution according to claim 1 or 4 wherein pervaporating the organic solvent is accomplished by flowing the organic solvent through a second hollow fiber bundle comprising a set of one or more nonporous hollow fiber tubes maintained under a vacuum to enable solvent to diffuse through the membrane while preventing the organic compounds from diffusing therethrough.

6. The process for continuously measuring the concentration of organic compounds in an aqueous solution according to claim 1 or 4 wherein pervaporating the organic solvent is accomplished by flowing the organic solvent through a second hollow fiber bundle comprising a set of one or more non-porous polymer hollow fiber tubes having a gas sweep on the outside thereof to enable solvent to diffuse through the tubes while preventing the organic compounds from diffusing therethrough.

7. An apparatus for continuously measuring the concentration of organic compounds in an aqueous solution comprising:

a first hollow fiber bundle comprising a set of one or more non-porous hollow fiber tubes;

means for allowing the outer surface of the first hollow fiber bundle to be placed in fluid flow relationship with an aqueous solution containing organic compounds therein;

a second hollow fiber bundle comprising a set of one or more non-porous hollow fiber tubes mountable in series with the first hollow fiber bundle;

means for allowing an organic solvent to flow through the first set of one or more nonporous hollow fiber tubes and then through the second set of one or more non-porous hollow fiber tubes;

means for pervaporating solvent flowing through the second set of one or more non-porous hollow fiber tubes to increase the concentration of organic compounds in said solvent;

means for measuring the flow rate of solvent which has exited said second hollow fiber bundle; and means for measuring the concentration of organic compounds in the solvent.

8. The apparatus for continuously measuring the concentration of organic compounds in an aqueous solution according to claim 7 further comprising a pump for forcing solvent through said first and second hollow fiber bundles.

9. The apparatus for continuously measuring the concentration of organic compounds in an aqueous solution according to claim 8 further comprising a means for measuring the flow rate of an organic solvent flowing through the first hollow fiber bundle.

10. The apparatus for continuously measuring the concentration of organic compounds in an aqueous solution according to claim 9 wherein said pump and said means for measuring the flow rate of an organic solvent flowing through the first hollow fiber bundle comprises a metering pump.

11. The apparatus for continuously measuring the concentration of organic compounds in an aqueous solution according to claim 10 further comprising a sampling pump for controlling the flow rate of an aqueous solution containing organic compounds which is placed in fluid flow relationship with the outer surface of the first hollow fiber bundle.

12. The apparatus for continuously measuring the concentration of organic compounds in an aqueous solution according to claim 7 or 10 wherein the means for pervaporating organic solvent comprises a gas sweep means for flowing gas over the second hollow fiber bundle to enable solvent therein to diffuse through the tubes and vaporize in said gas while preventing organic compounds from diffusing therethrough.

13. The apparatus for continuously measuring the concentration of organic compounds in an aqueous solution according to claim 12 wherein the gas sweep means for flowing gas over the second hollow fiber bundle comprises an air pump.

14. The apparatus for continuously measuring the concentration of organic compounds in an aqueous solution according to claim 7 or 10 wherein the means for pervaporating organic solvent comprises a vacuum means for creating low pressure on the outside of the second hollow fiber bundle enabling solvent to diffuse therethrough.

15. The apparatus for continuously measuring the concentration of organic compounds in an aqueous solution according to claim 7 or 10 wherein the means for measuring the concentration of organic compounds in the solvent consisting of one of a gas chromatograph, liquid chromatograph and ultra violet absorbance monitor.

* * * * *